(12) United States Patent
Yang

(10) Patent No.: US 10,383,843 B2
(45) Date of Patent: *Aug. 20, 2019

(54) USE OF TOTAL COUMARINS OF CNIDIUM FRUIT IN PREPARING MEDICAMENTS FOR TREATING PSORIASIS

(71) Applicant: Liping Yang, Guangzhou (CN)

(72) Inventor: Liping Yang, Guangzhou (CN)

( * ) Notice: Subject to any disclaimer, the term of this patent is extended or adjusted under 35 U.S.C. 154(b) by 639 days.

This patent is subject to a terminal disclaimer.

(21) Appl. No.: 13/956,378

(22) Filed: Aug. 1, 2013

(65) Prior Publication Data

US 2015/0038568 A1    Feb. 5, 2015

(51) Int. Cl.
*A61K 31/35* (2006.01)
*A61K 31/37* (2006.01)
*A61K 31/353* (2006.01)
*A61K 36/234* (2006.01)

(52) U.S. Cl.
CPC ............ *A61K 31/353* (2013.01); *A61K 31/35* (2013.01); *A61K 31/37* (2013.01); *A61K 36/234* (2013.01)

(58) Field of Classification Search
CPC ...... A61K 31/35; A61K 31/353; A61K 31/37; A61K 36/234
See application file for complete search history.

(56) References Cited

U.S. PATENT DOCUMENTS

2005/0123636 A1* 6/2005 Yang ...................... A61K 31/37
424/777

OTHER PUBLICATIONS

Matsuda et al., Jun. 2002, Biol. Pharm. Bull., vol. 25(6), pp. 809-812.*

* cited by examiner

*Primary Examiner* — Kara R McMillian
(74) *Attorney, Agent, or Firm* — George G. Wang; Bei & Ocean

(57) ABSTRACT

A pharmaceutic composition for treating an allergic skin disorder. It has an active component and a carrier. The active component has a major active ingredient osthol and a group of minor active ingredients: xanthotoxol, xanthotoxin, isopimpinellin, bergapten, and imperatorine. The major active ingredient osthol accounts for at least 90% by weight of the active component, which accounts for 5-35% by weight of the overall pharmaceutic composition.

15 Claims, No Drawings

USE OF TOTAL COUMARINS OF CNIDIUM FRUIT IN PREPARING MEDICAMENTS FOR TREATING PSORIASIS

CROSS-REFERENCE TO RELATED APPLICATION

This application is a continuation application of Ser. No. 13/355,532, filed on Jan. 21, 2012, which is a divisional application of application Ser. No. 10/505,015, filed on Jan. 18, 2005, which is now issued as U.S. Pat. No. 8,124,133, of which the content is incorporated herewith by reference.

FIELD OF THE INVENTION

The present invention relates to an extract of cnidium fruit and a use thereof, particularly total coumarins extracted from cnidium fruit as well as a use thereof in the treatment of psoriasis.

BACKGROUND OF THE INVENTION

Psoriasis is a kind of a chronic skin disorder most often positioned on the scalp, elbows, knees, and lower back of the patient, which presents silvery scales covering affected parts. The patient severely suffers from it. As a result, psoriasis significantly impacts patients' daily-life and work.

Recently a great number of patients have been suffering from psoriasis. However, psoriasis is very difficult to cure, and has been considered by the WHO one of the most important diseases to treat and prevent in the dermatological field.

The pathogeny of psoriasis has not been very clear. It is generally considered related with complicated factors such as heredity, infection, immunity, metabolizability, incretion, inflammation and psychological aspects.

Currently, it is the main way to treat psoriasis with medicaments though a lot of methods have been used. However, it is too difficult to avoid relapsing. By now cortical hormones or immunosuppressants have been used for the treatment (see: Progress of External Cortical Hormone Medicaments, Yaoxuetongbao, 1985, 20(9). Although the cortical hormone can reach a good short-term effect, it will make the epidermis and dermis of the affected part thinner, causes side effects such as induce telangiectasis and addiction of the medicaments and induces other complications, if used for a long time. Meanwhile, these medicaments cost expensive.

Chinese medicine cnidium fruit (also called "fructus cnidii" or "common cnidium fruit"), used for the treatment of diseases was recorded in ancient medical books. *Cnidium* fruit has been used in clinic for treating surgical, gynecological, dermatological and otolaryngological diseases such as lichen, scabies and scrotum eczema, because the Chinese believed that cnidium fruit has effect of "wetness-removing", "worms-killing" and "itch-stopping". However, there have been no reports on the treatment for psoriasis with total coumarins of an extract of cnidium fruit.

SUMMARY OF THE INVENTION

An object of the present invention is to provide total coumarins extracted from cnidium fruit, and another object of the present invention is to provide a use of the total coumarins defined herein in preparing a medicament to treat psoriasis, which has curative with little side-effect.

In the invention, the total coumarins of cnidium fruit are extracted from the fruit of *Cnidium monnieri* (L.) Cusson. Main components of the extract are coumarin compounds, which account for, over 85% by weight on the base of the extract. The total coumarins mentioned herein include six compounds of coumarin, in which Osthal is of the highest content, over 90% by weight. Osthal (compound VI) is a main active compound in the extract of cnidium fruit. All other five active compounds are furocoumarin, which have been identified xanthotoxol (compound I), xanthotoxin (compound II), isopimpinellin (compound III), bergapten (compound IV), imperatorine (compound V).

The coumarins described in the present invention have been identified and separated by HPLC, and UV absorption spectrum of the six coumarins showed osthal: $\lambda_{max}$ 322 nm (lgε=3.9); xanthotoxol: $\lambda_{max}$ 250 nm (lgε=4.25); xanthotoxin: $\lambda_{max}$ 248 nm (lgε=4.4); isopimpinellin: $\lambda_{max}$ 268 nm (lgε=4.26); bergapten: $\lambda_{max}$ 249 nm (lgε=4.38); and imperatorin: A$\lambda_{max}$ 249 nm (lgε=3.65).

According to the theory that the UV absorption spectrum of all coumarinsis can be combined to calculate the amount of the coumarins, the UV absorption spectrum of the total coumarins in ethanol has been given.

11 batches of extracts of cnidium fruit have been identified through UV in ethanol in the present invention and the result showed that they had almost the same absorption spectrum. The maximum absorption of all the extracts was at around 322 nm (from 319 nm to 326 nm) with a flat peak, and other peaks were at 250 nm, 255 nm, and 265 nm, respectively.

The present invention relates to a use of total coumarins in preparing a medicament to treat psoriasis, and particularly to a use of a Chinese traditional medicine cnidium fruit in treating psoriasis. In the invention, the medicament comprises 5-35% total coumarins by weight and a pharmaceutically acceptable carrier and/or excipient.

The various features of novelty which characterize the invention are pointed out with particularity in the claims annexed to and forming a part of this disclosure. For a better understanding of the invention, its operating advantages, and specific objects attained by its use, reference should be made to the following description in which there are illustrated and described preferred embodiments of the invention.

DETAILED DESCRIPTION OF PARTICULAR EMBODIMENTS OF THE INVENTION

The preparation of total coumarins involved in the present invention is as follows:

*Cnidium* fruit was ground to be powder. The powder was extracted with 80-95% ethanol at 60-80° C. for two hours, and filtered. The residue then was extracted twice with 80-95% ethanol. The filtrates were combined and kept at room temperature for at least 16 hours, and filtered to obtain a green precipitate. Further precipitate was obtained by concentrating the filtrate. The total coumarins of the invention were then obtained after the precipitate was dried.

1. Effect of Total Coumarins on Mitosis of Vaginal Epithelial Cells in Mice 60 female NIH mice of 27 g±2 g were selected. After being intraperitoneally injected with diethylstilbesrolum for 3 days continuously, 0.2 mg/day for each animal, all the mice were left in estrum interval. From the 4th day, the mice were randomly divided into four groups, 15 mice each. The mice of the four groups were administrated for three days by gavage with 150 mg/kg of total coumarins, 75 mg/kg of total coumarins, 15 mg/kg of anthralin and 15 ml/kg of physiological saline, respectively, once one day. The last administration was carried out at 8:00 am in order to avoid the interference of various administration rhythms between day and night in the mice to the test result. At 9:00 am, 2 mg/kg of colchicine was injected to the mice to make the mitosis of vaginal epithelial cells stopped at the middle cycle of M phase.

The mice were killed at 2 pm. A sample from the vagina of the animal was taken out and fixed in a 10% formaldehyde solution. A slice of tissue was observed under an optical microscope. The number of mitosis per 300 fundus cells was counted to obtain an average number of mitosis among 100 fundus cells, which was regarded as the index of mitosis of vaginal epithelial cells.

The result of the test was given in Table 1. It showed that the total coumarins of the invention had significant inhibition against mitosis of vaginal epithelial cells in mice.

TABLE 1

| Groups | Doses (mg/kg) | Mice | Index of Mitosis % |
| --- | --- | --- | --- |
| Total Coumarins | 150 | 15 | 11.3 ± 2.0* |
| Total Coumarins | 75 | 15 | 19.8 ± 2.8** |
| Anthralin | 15 | 15 | 13.4 ± 2.1* |
| Physiological Saline | 15 ml | 15 | 22.2 ± 2.4 |

*$P < 0.01$;
**$P < 0.05$ vs. Physiological Saline Group

2. Effect of Ointments of Total Coumarins on Formation of Stratum Granulosum Epidermidis in Rats Tail Scale 40 SD rats, 180 g±10 g, were divided randomly into four groups, of which one group was anointed with an ointment prepared by total coumarins of the invention onto the tail, with a dosage of 0.3 g for each rat, and once per day; and another group was anointed with the same ointment and the same dosage, but twice per day. The third group was anointed with an ointment prepared by anthralin with the same dosage, twice per day, and the fourth group was anointed with a blank ointment, twice per day. After the ointment was continuously anointed onto the tail for 20 days, the rats were killed.

A piece of dorsal skin of the rat about 1.5 cm far from the tail root was cut down. The dorsal skin was prepared as a tissue slice, which was observed under an optical microscope. The number of the squama that had consecutive granular cells of stratum among 100 squamae in the epidermis at the rat tail was obtained. The result was given in Table 2. It showed that the ointment made of total coumarins could greatly increase the number of squamae that had epidermal granular cells of stratum at the rat tail.

TABLE 2

| Groups | Doses (g/rat) | Rats | Number of Squamae Having Granular Layer Cells (%, x ± SD) |
| --- | --- | --- | --- |
| Coumarins Ointment | 0.3 | 10 | 25.36 ± 9.28* |
| Coumarins Ointment | 0.3 | 10 | 18.45 ± 8.78** |
| Anthralin Ointment*** | 0.3 | 10 | 21.76 ± 8.51* |
| Blank Ointment | 0.3 | 10 | 10.87 ± 5.64 |

*$P < 0.01$;
**$P < 0.05$;
***once one day

3. Inhibition of Passive Cutaneous Anaphylaxis (PCA) of Rats

Hair on the back of 40 SD rats, 180 g±10 was shaved off. 0.2 ml of a diluted rat-antiserum (1:10) was hypodermically injected into each rat through two places on the back, 0.1 ml for each place. After being injected, the rats were di vided randomly into four groups, which were administered by gavage with 75 mg/kg of total coumarins, 150 mg/kg of total coumarins, 15 mg/kg of anthralin and 15 ml/kg of distilled water for 3 days, once per day. After the injection with the rat-antiserum 48 hours, 1 ml of 0.5% evans blue, as an antigen, was intravenously injected into the rats through the caudal vein. The rats were killed in 20 minutes. A piece of skin with blue speckles was taken out from the back, and immersed in 5 ml solution of acetone/physiological saline (acetone:physiological saline=7-3 v/v) for 24 hs. After centrifugation; the supernatant was taken for measuring the optical density (OD) at 590 nm. Inhibition rate was obtained in accordance with the following equation. The result was given in Table 3. It showed that total coumarins had a significant inhibitory effect on passive cutaneous anaphylaxis (PCA) of rats.

Inhibition (%)=[OD(control)−OD(drug)]× 100%/OD(control)

TABLE 3

| Groups | Doses (mg/kg) | Animals | OD | Inhibition (%) |
| --- | --- | --- | --- | --- |
| Total Coumarins | 150 | 15 | 0.029 ± 0.018* | 67.42 |
| Total Coumarins | 75 | 15 | 0.045 ± 0.027** | 49.44 |
| Anthralin | 15 | 15 | 0.043 ± 0.25* | 51.69 |
| Physiological Saline | 15 ml | 15 | 0.089 ± 0.41 | |

*$P < 0.01$,
**$P < 0.05$ vs Physiological Saline Group

4. Inhibition of Total Coumarins on Ear-Swelling of Mouse Induced by Croton Oil

80 NIH mice, 27±2 g, were divided randomly into four groups, which were anointed at the auricle of both ears with 50 ul of a croton oil composition composed of 2% croton oil by weight, 5% water, 20% ethanol and 73% ether by weight. 0.5 hour later, the mice of four groups were respectively anointed at the left auricle with 0.15 g and 0.3 g of an ointment prepared by total coumarins, with 0.3 g of a blank ointment, and with 0.3 g of an ointment prepared by anthralin.

After 4 hours of the treatment, the mice were killed. A piece of ear in diameter of 9 mm was taken out from both two auricles of each mouse, and weighted. The difference of the weight between the two ears was regarded as the degree of ear-swelling.

The result was listed in Table 4, which showed that the ointment prepared by the total coumarins had a significant inhibition on the swelling at the mouse ear induced by croton oil.

TABLE 4

| Groups | Doses (g/ear) | Animals | Differences between Ears (mg) |
| --- | --- | --- | --- |
| Coumarins Ointment | 0.3 | 20 | 1.52 ± 0.76* |
| Coumarins Ointment | 0.15 | 20 | 0.93 ± 0.68** |
| Anthralin Ointment | 0.3 | 20 | 0.95 ± 0.71** |
| Blank Ointment | 0.3 | 20 | 0.49 ± 0.25 |

*$P < 0.01$,
**$P < 0.05$, vs Blank Ointment Group

5. Inhibitory Effect on the Swelling of Rat Toes Induced by Egg-Write Injection

50 SD rats, 150 g±10 g, were divided randomly into five groups. The volume of the toes at the same side of rats among the 5 groups was measured. 10% of egg white was injected into the toes, 0.2 ml each toe. After that, rats of two groups were anointed respectively with 0.15 g and 0.3 g of an ointment of total coumarins (containing 10% total coumarins) at each toe. Rats of other two groups were respectively anointed with 0.3 g of a blank ointment and 03 g of an ointment of anthralin at each toe. The rest one group was treated nothing as a control. 0.5 hour later, the above treatment was repeated. At 1st, 2nd, 4th, and 6th hour the volume of the toes were measured. The difference of the volume was regarded as the degree of the swelling of the toes. The result was showed in Table 5.

Table 5 showed that an ointment of total coumarins could inhibit the swelling at the mouse toes (paws) induced by egg-white.

TABLE 5

| Groups | Doses (g/ear) | Animals | Degree of Ear-Swelling (ml) | | | |
|---|---|---|---|---|---|---|
| | | | 1 h | 2 h | 4 h | 6 h |
| Coumarins Ointment | 0.15 | 10 | 0.401 ± 0.210* | 0.336 ± 0.183* | 0.371 ± 0.167* | 0.354 ± 0.152* |
| Coumarins Ointment | 0.3 | 10 | 0.324 ± 0.181** | 0.308 ± 0.168** | 0.290 ± 0.146** | 0.290 ± 0.146** |
| Anthralin | 0.3 | 10 | 0.408 ± 0.201* | 0.391 ± 0.209* | 0.375 ± 0.189** | 0.351 ± 0.165* |
| Blank Ointment | 0.3 | 10 | 0.584 ± 0.205 | 0.579 ± 0.198 | 0.554 ± 0.186 | 0.528 ± 0.181 |
| Control | | 10 | 0.612 ± 0.207 | 0.608 ± 0.214 | 0.591 ± 0.195 | 0.486 ± 0.104 |

*$P < 0.05$,
**$P < 0.01$ vs Control Group

6. Anti-Itching Effect on Guinea Pin Induced by Histamine Phosphate 50 guinea pigs, 250 g±15 g, were divided randomly into five groups. Right toes of the animal were shaved off. Animals of two groups were anointed respectively with 0.15 g and 0.3 g of an ointment of total coumarins (containing 10% total coumarins) at each toe. Animals of two groups were respectively anointed with 0.3 g of an ointment without total coumarins and 0.3 g of an ointment of anthralin at each toe. The rest group was treated nothing as a control.

The skin where the hair was shaved off was scratched with 1# sand-paper next day until some extravasate exuded. The above treatment was then repeated. After 10 minutes, 0.01% of a histamine phosphate solution with a successive concentration starting at 0.01%, 0.02%, 0.03% was dropped onto the scratched toe at an interval of 3 minutes (0.05 ml each time) until the guinea pig began to lap up the toe. The dosage of the histamine when the guinea pig lapped up the toe was regarded as a threshold of itch-causing. The result was given in Table 6, which showed that the ointment of total coumarins could significantly increase the threshold of itch-causing of the guinea pig induced by histamine phosphate.

TABLE 6

| Groups | Doses (g/toe) | Animals | Itching Threshold (ug) |
|---|---|---|---|
| Coumarins Ointment | 0.15 | 10 | 142.75 ± 120.15* |
| Coumarins Ointment | 0.3 | 10 | 206.25 ± 111.60** |
| Anthralin Ointment | 0.3 | 10 | 158.50 ± 131.48* |

TABLE 6-continued

| Groups | Doses (g/toe) | Animals | Itching Threshold (ug) |
|---|---|---|---|
| Blank Ointment | 0.3 | 10 | 38.75 ± 20.14 |
| Control | | 10 | 37.50 ± 25.00 |

*$P < 0.05$,
**$P < 0.01$ vs Control Group

7. Clinical Trial

Methods: Comparing effect of total coumarins on psoriasis with that of anthralin in patients. An ointment containing 10% total coumarins was anointed onto psoriasis at one place of a patient and an ointment of anthralin was anointed onto psoriasis at another place of the identical patient (as positive control), for 30 days, one or two times one day. No other relevant drugs were treated during the trial.

Assay Standard of Treatment: Four degrees applied according to the Standard on Dermatosis prescribed by the National Ministry of Health The result as given in Table 7 showed that the clinic curative rate reached 60% and the total effective rate reached 96.7%.

TABLE 7

| Groups | Patients | Curative | Effective | Effective | Not-Effective | Totally Effective |
|---|---|---|---|---|---|---|
| Coumarins Ointment | 30 | 18 | 9 | 2 | 1 | 96.7% |
| Anthralin Ointment | 30 | 12 | 16 | 2 | 0 | 100% |

8. Acute Toxicity

Oral Experiment

After being fasted for 16 hrs, 100 NIH mice, 19±1 g, half male and half female, were divided randomly into 10 groups, each of which contained 10 mice. The ratio of consecutive dosage between each group was 1:0.75. Each mouse was administered by gavage with 0.8 ml for one time. The daily clinical sign of toxicity and the number of death were observed for 14 days. LD50 and the available range of 95% according to the method of Bliss were calculated. The result showed as follows: LD50 (male)=463.90 mg/kg, the available range of 95% was 406.16-529.86 mg/kg; and LD50 (female)=409.85 mg/kg, the available range of 95% was 357.02-470.50 mg/kg. The animals that survived the experiment were in fairly good condition with normal appetite and put on weight respectively.

External Experiment:

(1) Acute Toxicity Test on Scratched Skin of Rabbits 16 rabbits (NZR) were denuded at the dorsal back for 150 cm2. 24 hours later, the naked skin was scratched with 11 sand paper until the tissue fluid effused. Then, the 16 rabbits were divided randomly into four groups (half were male). The rabbits of three groups were respectively anointed with an ointment containing 10%, 20%, and 30% of total coumarins, 3 g for each, and those of the other were anointed with an ointment without total coumarins, 5 g for each. A piece of oil paper and gauze were used to cover the treated skin. The anointed materials were removed 24 hours later. The common condition of the animals was observed for 7 days. The result showed that no rabbits died and the common condition of the rabbits including eating, activity, and bowel movement etc. was kept in the normal way.

(2) Acute Toxicity Test on Normal Skin of Rabbits

An acute toxicity test on the normal skin of rabbits was conducted in the same way as described in Test (1). The result showed that there was no death in all the four groups. After the treatment the animals were in good condition and there were no obvious different changes in actions and discharges, with normal appetite and the common condition of the rabbits including eating, activity, and bowel movement etc. was kept in the normal way.

Conclusion

The acute toxicity test on both the normal and the scratched skin of the rabbits showed that no toxicity to the animals with the treatment of total coumarins (10%, 20% and 30%).

9. Chronic Toxicity 3 groups of rats were divided into High, Medium and Low dosal groups and were administrated with total coumarins, 250 mg/kg, 158 mg/kg and 100 mg/kg for 90 days. As a result, one group of the rats were treated noting as a blank control. The common condition of the rats was observed, and the hematology and serum clinical chemistry were evaluated. The result showed that all the animals presented as normal except two rabbits in the group administrated with 250 mg/kg died and other rats in this group increased in body weight slower than those in other groups.

The above experiments show the following advantages of the present invention.

(1) Total coumarins of cnidium fruit of the invention can significantly inhibit mitosis of vaginal epithelial cells in mice.

(2) Total coumarins of cnidium fruit of the invention can greatly promote the formation of epidermal granular stratum in rat tail's scales, and has a strong inhibitory effect on passive cutaneous anaphylaxis of rats.

(3) It can reduce ear-swelling of mouse induced by croton oil as well as foot-swelling of rats caused by egg-white.

(4) Anti-itching experiment on guinea pigs shows that the ointment of the invention can lessen the reaction of itching.

(5) It is confirmed that the total coumarins can stimulate keratode reduction and have effect of anti-inflammation, anti-anaphylaxis, anti-allergy and fungus-killing.

(6) Total coumarins extracted from cnidium fruit are safe to use, and have strong pharmacological activity with multiple components. It can be administrated both externally and orally.

(7) Total coumarins of the invention can improve the clinical symptom of the psoriasis patient and increase the curative rate (60%, 96.7% of the total efficiency).

(8) Materials used in the present invention can be got form a plenty of sources.

Medicaments of the invention can be prepared in various formulations such as capsules, syrups, injections, ointments, creams, suppositories, tinctures and so on.

The invention will be further described with the following examples

Example 1

1 kg of fruit of *Cnidium monnieri* (L.) Cusson was powdered, and then dissolved in 6 kg of 85% ethanol. The mixture was maintained at 80° C. for 2 hours, and filtered. The residue was extracted twice with 3,000 ml of 85% ethanol at 80° C., each for 2 hours. All filtrates were combined and kept at room temperature. Colorful precipitate was collected by filtration. The filtrate was then concentrated at 80° C. under reduced pressure until the concentration of ethanol in the filtrate reached 45% and kept at room temperature. After 24 hours, green precipitate was collected and dried at 60° C. to obtain an extract of total coumarins, yield 1.2%.

Example 2

1 kg of fruit of *Cnidium monnieri* (L.) Cusson was powdered, and then dissolved in 5 kg of 95% ethanol. The mixture was maintained at 60° C. for 2 hours, and filtered. The residue was extracted twice with 3,000 ml of 95% ethanol at 60° C., each for 2 hours. All filtrates were combined and kept at room temperature. Colorful precipitate was collected by filtration. The filtrate was then concentrated at 60° C. under reduced pressure until the concentration of ethanol in the filtrate reached 45% and kept at room temperature. After 24 hours, green precipitate was collected and dried at 80° C. to obtain an extract of total coumarins, yield 1.2%.

Example 3

An ointment of oil in water was prepared with total coumarins obtained in Example 1 and other components: total coumarins 100 g, Stearic acid 80 g, glyceryl monostearate 100 g, white vaseline 80 g, glycerin 160 g, Tween-80 60 g, water 280 g, and glycerin and water (4:10) were added to 1,000 g. The ointment prepared was even and smooth, without irritation to the skin.

Example 4

100 g of total coumarins prepared in Example 1 was, mixed with starch, and wetted with a little amount of ethanol. The mixture was granulated after mixed uniformly, and dried. Then, 1,000 tablets were prepared by tableting the granules, coating and polishing the same using a conventional method after a lubricant was added. Each tablet contained 0.1 g of the total coumarins.

Example 5

300 g of total coumarins prepared in Example 2 was mixed with starch, and wetted with a little amount of ethanol. The mixture was granulated after mixed uniformly, and dried. Then, 1000 tablets were prepared by tableting the granules, coating and polishing the same using a conventional method after a lubricant was added. Each tablet contained 0.3 g of the total coumarins.

Example 6

250 g of total coumarins as prepared in Example 2 was ground into fine powder and sieved. The sieved powder, encapsuled. 1,000 of capsules were prepared, each containing 0.25 g of the total cumarins.

Example 7

109 of total coumarins prepared in Example 1 was dissolved in 10 ml of benzyl alcohol and 10 ml of Tween-80.

To the mixture was added injection water to reach 2,000 ml. The solution was filtered, sterilized, and bottled with 2 ml each. The injection per milliliter contained 5 mg of the total coumarins.

Example 8

20 g of total coumarins prepared in Example 2 was dissolved in 200 ml benzyl alcohol and, 20 ml of propylene glycol. To the mixture was added injection water to reach 2,000 ml. The solution was, filtrated, sterilized, and bottled with 2 ml each. The injection per milliliter contained 10 mg of the total coumarins.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of anti-itching, comprising a step of administering to a human subject suffering from a symptom of skin itching a pharmaceutically effective amount of a pharmaceutical composition comprising an active component and a carrier, wherein said active component comprises a major active ingredient and a group of minor active ingredients, said major active ingredient is osthol which accounts for at least 90% by weight of said active component.

2. The method of claim 1, wherein said active component accounts for 5-35% by weight of said pharmaceutical composition.

3. The method of claim 2, wherein said group of minor active ingredients comprises a pharmaceutically effective amount of each xanthotoxol, xanthotoxin, isopimpinellin, bergapten, and imperatorine.

4. The method of claim 3, wherein said pharmaceutical composition is in a dosage form of an ointment.

5. The method of claim 3, wherein said pharmaceutical composition is in a dosage form of a tablet.

6. The method of claim 3, wherein said pharmaceutical composition is in a dosage form of an injection.

7. The method of claim 1, wherein said group of minor active ingredients comprises a pharmaceutically effective amount of xanthotoxol.

8. The method of claim 1, wherein said group of minor active ingredients comprises a pharmaceutically effective amount of xanthotoxin.

9. The method of claim 1, wherein said group of minor active ingredients comprises of isopimpinellin.

10. The method of claim 1, wherein said group of minor active ingredients comprises a pharmaceutically effective amount of bergapten.

11. The method of claim 1, wherein said group of minor active ingredients comprises a pharmaceutically effective amount of imperatorine.

12. The method of claim 1, wherein said group of minor active ingredients comprises a pharmaceutically effective amount of each xanthotoxol, xanthotoxin, isopimpinellin, bergapten, and imperatorine.

13. The method of claim 1, wherein said pharmaceutical composition is in a dosage form of an ointment.

14. The method of claim 1, wherein said pharmaceutical composition is in a dosage form of a tablet.

15. The method of claim 1, wherein said pharmaceutical composition is in a dosage form of an injection.

* * * * *